United States Patent [19]

Jones

[11] Patent Number: 4,530,706
[45] Date of Patent: Jul. 23, 1985

[54] RESPIRATOR CARTRIDGE END-OF-SERVICE LIFE INDICATOR

[75] Inventor: John A. Jones, Wilbraham, Mass.

[73] Assignee: American Optical Corporation, Southbridge, Mass.

[21] Appl. No.: 312,201

[22] Filed: Oct. 19, 1981

[51] Int. Cl.³ ............................................. B01D 50/00
[52] U.S. Cl. ........................................ 55/275; 55/379; 55/316; 55/DIG. 34; 55/DIG. 35
[58] Field of Search ................. 55/387, 275, 316, 274, 55/DIG. 34, DIG. 35; 422/86, 120; 128/205.27

[56] References Cited

U.S. PATENT DOCUMENTS

| | | | |
|---|---|---|---|
| 1,537,519 | 5/1925 | Yablick | 55/DIG. 34 |
| 2,614,650 | 10/1952 | Chandler et al. | 55/275 |
| 3,029,581 | 4/1962 | Robbins | 55/389 |
| 3,171,726 | 3/1965 | Roney et al. | 55/275 |
| 3,377,294 | 4/1968 | Davis et al. | 55/275 |
| 3,892,549 | 7/1975 | Lyshkow | 55/316 |
| 3,966,440 | 6/1976 | Roberts | 55/274 |
| 4,154,586 | 5/1979 | Jones et al. | 55/274 |

FOREIGN PATENT DOCUMENTS 644230  7/1962  Canada ................................. 55/275

*Primary Examiner*—Bernard Nozick
*Attorney, Agent, or Firm*—Anthony M. Lorusso; George A. Loud

[57] ABSTRACT

Visual indication of respirator cartridge end-of-service life is accomplished with color indicator means particularly designed for long term shelf life and an adaptability to respond to both water soluble and water insoluble organic vapors.

9 Claims, 3 Drawing Figures

RESPIRATOR CARTRIDGE END-OF-SERVICE LIFE INDICATOR

BACKGROUND OF THE INVENTION

1. Field of the Invention

This invention relates to respirator cartridges and has particular reference to improvements in end-of-service life indicators for organic vapor/gas filters.

2. Description of the Prior Art

Respirators using replaceable filter cartridges are commonly used for protection against a wide range or respiratory hazards which include toxic and/or disease producing dusts, mists, sprays, fumes, vapors or gases. The cartridges are replaced when their capacity to provide respiratory protection at or below hazardous concentration levels becomes apparent to the user or is otherwise arbitrarily or administratively determined.

As discussed in U.S. Pat. No. 4,154,586, windowed color changing indicators provide desirable means for monitoring the effectiveness of organic vapor respirator cartridges.

Heretofore, however, the shelf life of color indicators, e.g. of the type disclosed in U.S. Pat. No. 4,154,586, has been considerably shorter than that of the main cartridge sorbent. This, in addition to promoting premature disposal of the cartridges, i.e. while still having a useful absorbency to toxic vapors or gases, further requires costly inventory monitoring based upon useful life expectancies of the indicator chemicals per se.

Accordingly, a principal object of the present invention is to improve the shelf life of indicator systems and respirator cartridges with the corollary of extended cartridge usefulness and avoidance of cartridge use with spent or partially spent end-of-service life indicators.

Another object is to accomplish the above with end-of-service life indicating system improvement, e.g. improvement in the indicator system's ability to respond to both water soluble and water insoluble organic vapors.

Still another object is to accomplish faster than heretofore and more complete indicator system color change for a wide variety of organic vapors; and Yet another object is to afford color indicator moisture protection during periods of cartridge non-use.

Other objects and advantages of the invention will become more readily apparent from the following description.

SUMMARY OF THE INVENTION

The foregoing objectives and their corollaries are accomplished with upstream molecular sieving of atmospheres directed through color indicating chemicals of respirator cartridge units of the type discussed above.

By such means, moisture molecules are removed from vapors to be monitored so that the "dried" vapors can make immediate contact with color indicating (oxidizing) chemicals upon reaching same. Faster than usual and more complete chemical color change results with exposure to either water soluble or water insoluble vapors.

In addition to so lending the present system sensitive to a greater than usual variety of organic vapors, previously used color indicator catalysts are eliminated for avoidance of heretofore indicator system deterioration which will be discussed in detail hereinafter.

Exposure of the present color change chemicals to moisture by air diffusion during cartridge shelf time or other non-use is avoided by provision of a drying agent adjacent to the upstream side of the color change chemicals.

BRIEF DESCRIPTION OF THE DRAWINGS

Details of the invention will become more readily apparent from the following description when taken in conjunction with the accompanying drawings in which.

DESCRIPTION OF THE PREFERRED EMBODIMENTS

Figure 1:
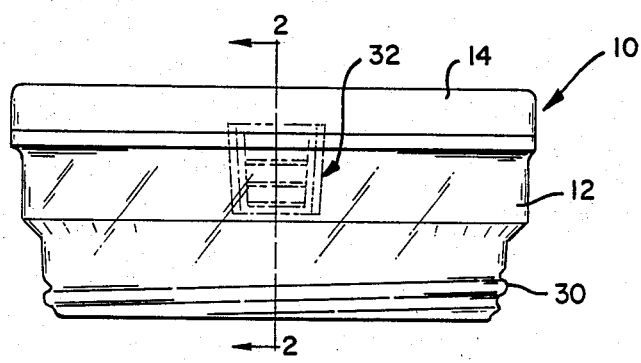
FIG. 1 is a side elevational view of an organic vapor-gas respirator cartridge embodying an end-of-service life indicator system according to the invention.

Referring to the drawings, organic vapor/gas filtering cartridge 10 comprises shell 12 having cover 14, either or both of which may be formed in conventional fashion of metal such as aluminum or a molded plastic material which is either transparent or opaque. Also, in the usual fashion of such construction, cartridge 12 is filled with an adsorbent 16, e.g. activated charcoal.

Top and bottom woven or loosely felted pads 18 and 20 conventionally prevent escape of particles of adsorbent 16 while allowing free passage of air and/or vapors therethrough. Perforations 22 and 24 in cover 14 and shell 12 respectively admit air and vapors to be filtered and allow passage of filtered air out of cartridge 10. Arrows 26 indicate passage of air and vapors or gases into cartridge 10, i.e. into the upstream side of the cartridge, while arrows 28 illustrate emission of filtered air from the downstream side of cartridge 10.

As it is well known in the art, respirator cartridges of the type illustrated are downstream threaded into face masks for reception of the filtered atmosphere 28 by wearers of the mask. Rolled, molded or otherwise formed threads 30 serve this purpose.

While it will become apparent hereinafter that the present invention is adaptable to various other forms of respirator cartridges, those interested in details of replaceable respirator cartridge adaptors and face masks may refer to U.S. Pat. Nos. 2,744,525 and 3,966,440.

Referring more particularly to the crux of the present invention, end-of-service life indicator 32 comprises transparent capsule 34 molded or otherwise formed of a suitable plastic material. A Kodar polyester such as that commercially identified as PETG6763 by Eastman Chemical Products of Kingsport, Tenn., U.S.A., may be used.

Figure 2:
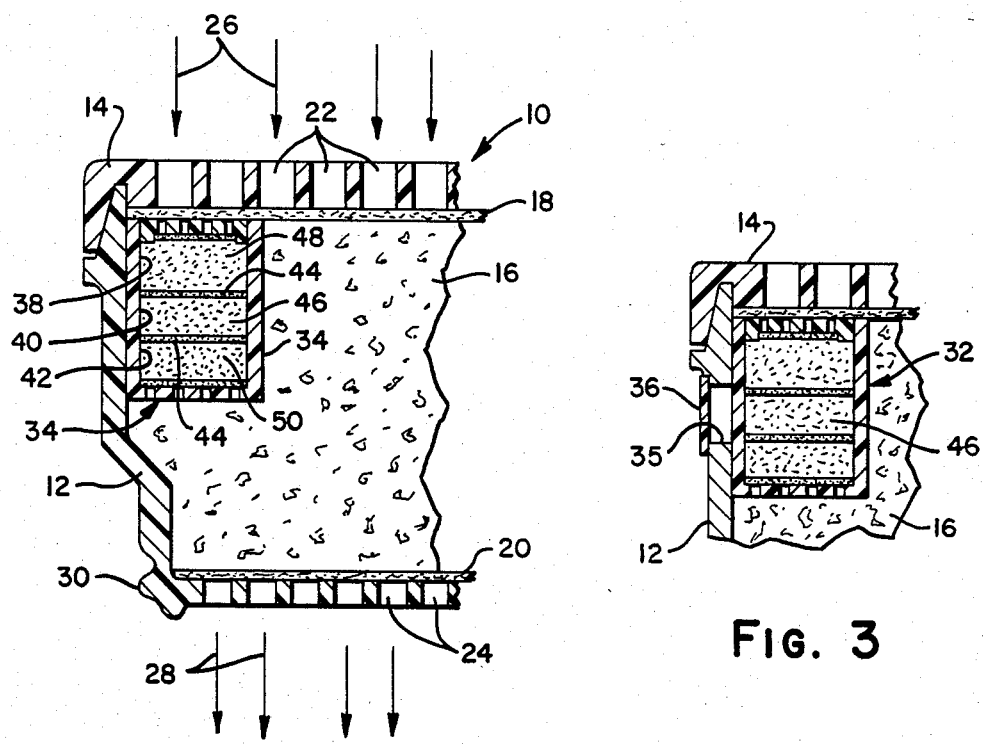
FIG. 2 is an enlarged fragmentary cross-sectional view of the cartridge taken generally along line 2—2 of FIG. 1.
Figure 3:
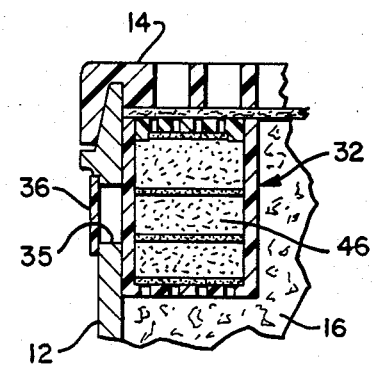
FIG. 3 is a similar fragmentary cross-sectional view of a modification of the cartridge of FIGS. 1 and 2.

Capsule 34 is positioned interiorally of cartridge 10 adjacent its upstream side and against shell 12 for viewing through the shell wall. As illustrated in FIGS. 1 and 2, shell 12 is formed of a transparent material which allows such viewing of capsule 34. Alternatively, an opening 35, covered with a transparent window 36 may be provided in shell 12 as illustrated in FIG. 3. Other forms of shell windowing may, of course, be used.

Capsule 34 is perforated at top and bottom and preferably internally divided into three superimposed compartments 38, 40 and 42 separated from each other by thin fill pads 44 which permit free passage of air, vapors and/or gases therethrough. These pads may be formed of woven or loosely felted materials in a fashion similar to the construction of fill pads 18 and 20 but of a considerably smaller size.

Intermediate compartment 40 of capsule 34 is filled with color change indicator material 46, e.g. a dried solution of a reagent grade sodium dichromate in sulfuric acid and water supported by granular silica gel. Those interested in details of such an indicator and/or method of its preparation may refer to U.S. Pat. No. 4,154,586. It should be understood, however, that the present invention is not intended to be limited to specific details of indicator composition. Compartment 40 may be filled with any indicator material known to react with a similar visual color change when contacted by molecules of organic vapors or gases of which Tetrahydrofuran, Ethylene Glycol Momethyl Ether, Toluene, N-Octane, N-Butyl Alcohol and Carbon Disulfide are exemplary.

For purposes of enhancing the color change activity and display function of indicator material 46 and further rendering same responsive to both water soluble and water insoluble organic vapors, upstream compartment 38 is filled with molecular sieve material 48, e.g. 14–30 Mesh (U.S. Sieves Standard), preferably having a nominal pore size of 4 Angstroms with moisture content of less than 1.5% wt. A material presently commercially available is catalogued as Grade 516 by Davidson Chemical Division, W. R. Grace and Company, Baltimore, Md. Sieve material in powdered form of approximately 4 Angstrom pore size may also be used.

Sieve material 48, in functioning to selectively adsorb molecules in the 4 Angstrom size (e.g. $H_2O$) over larger molecules, "dries" vapors or gases entering capsule 34 thereby affording immediate intimate contact between the vapor/gas molecules and the oxidizing color change indicator material 46. Thus, considerably faster and more complete color change than heretofore is effected for both water soluble and water insoluble organic vapors with the corollary of greater personal safety, i.e. readily identified color indication of end of cartridge service life is provided.

The water adsorption function of upstream sieve material 48, i.e. keeping vapors and gases reaching indicator material 46 "dry", extends the heretofore life (including shelf life) of indicator 32 and consequently that of cartridge 10. Additionally, downstream compartment 42 is preferably filled with a drying agent 50, e.g. silica gel. By such means, exposure of indicator material 46 to moisture due to air diffusion during periods of cartridge 10 non-use is avoided. A suitable silica gel is Grade 408, 12–29 Mesh (Tyler Sieve) having a density of approximately 47 lbs. per ft.$^3$. Davidson Chemical Division, W. R. Grace and Company, Baltimore, Md. is presently a supplier.

It is pointed out that the color indicator system of this invention avoids the heretofore need for catalytic agents which, over extended periods of time, have been known to attack plastic container materials causing clouding thereof and partial masking of visual perception of indicator color change.

The following data illustrates the results of comprehensive testing of the invention with a 105 ML fill of adsorbent 16 using a vapor flow rate of 32 LPM in concentration of 1,000 ppm at a temperature of 25° C. with 50% relative humidity wherein:

Threshold Limit Value (TLV) Concentration = the time-weighted average concentration for a normal 8-hour workday or 40-hour workweek, to which nearly all workers may be repeatedly exposed, day after day, without adverse effect.

Service Life = the elapsed time from the start of the input flow through a test cartridge to the time that 5 ppm of vapor appears in the cartridge effluent regardless of TLV.

| VAPOR | TLV CONC. (ppm) | SERVICE LIFE (MINUTES) | INDICATOR COLOR CHANGE (MINUTES) |
|---|---|---|---|
| Tetra-hydrofuran | 200 | 44.5 | 44.5 |
| | | 55.9 | 53.0 |
| | | 43.0 | 49.0 |
| Ethylene Glycol Momethyl Ether | 25 | 129.0 | 34.5 |
| | | 116.8 | 25.0 |
| | | 115.0 | 42.0 |
| Toluene | 200 | 100.0 | 15 |
| | | 111.6 | 12 |
| | | 120.2 | 15 |
| N—Octane | 500 | 71.6 | 21 |
| | | 78.1 | 21 |
| | | 87.1 | 21 |
| N—Butyl Alcohol | 100 | 145.0 | 130 |
| | | 148.8 | 130 |
| | | 151.4 | 130 |
| Carbon Disulfide | 20 | 54.9 | 52 |
| | | 55.8 | 52 |
| | | 56.0 | 52 |

It should be apparent from the foregoing that indicator 32 of the present invention is readily adaptable to various types and/or forms of respirator cartridges or canisters other than that illustrated in the present drawings i.e. various modifications and adaptations of the precise mechanical and chemical forms of the invention here shown and described may also be made to suit particular requirements. Accordingly, the foregoing illustrations are not to be interpreted as restrictive of the invention beyond that necessitated by the following claims.

I claim:

1. In a respirator cartridge having a covered shell with oppositely disposed upstream and downstream perforated sides for passage of air therethrough, the combination of an adsorbent for an organic vapor/gas supported between said perforated sides and an end-of-service life indicating system within said adsorbent adjacent said upstream side of said shell including an indicator characterized to undergo a change of color concomitant with exposure to concentrations of organic vapors and gases which are below a threshold limit known to be safe to inhale, said indicating system including the improvement of molecular sieve material between said indicator and said perforated upstream side of said covered shell with said sieve material adjoining said indicator for adsorbing molecules of matter within a range of molecular size including those of $H_2O$ while permitting passage of larger molecules of organic vapors and gases for rendering said larger molecules passed through adaptable to intimate contact with said indicator and immediate reaction therewith.

2. The improvement according to claim 1 wherein said molecular sieve is of 14–30 Mesh (U.S. Sieves Standard) with nominal pore size of approximately 4 Angstroms.

3. The improvement according to claim 1 further including a drying agent adjacent to said indicator at a side thereof opposite to said disposition of said molecular sieve, said drying agent separating said indicator from said adsorbent.

4. The improvement according to claim 1 wherein said indicating system includes a closed capsule having perforated top and bottom sides respectively facing upstream and downstream of said covered shell, said capsule top being positioned adjacent to said upstream side of said shell and said molecular sieve and indicator being disposed within the capsule, the former being adjacent said side of said capsule facing upstream of said shell.

5. The improvement according to claim 4 further including a drying agent in said capsule adjacent said side of said capsule facing downstream of said shell, said indicator being between said molecular sieve and drying agent, said drying agent separating said indicator from said adsorbent.

6. The improvement according to claim 5 wherein said drying agent is silica gel.

7. The improvement according to claim 4 wherein said capsule is transparent and disposed against an internal side of said shell, said side of said shell affording windowed exposure of said capsule.

8. The improvement according to claim 7 wherein said shell is formed of a transparent material so as to afford said windowed exposure of said capsule.

9. The improvement according to claim 7 wherein said shell is provided with an opening adjacent to said capsule to afford said windowed exposure of said capsule.

* * * * *